(12) United States Patent
Williams et al.

(10) Patent No.: US 7,504,069 B2
(45) Date of Patent: Mar. 17, 2009

(54) MICRO DEVICE FOR HIGH RESOLUTION DELIVERY AND MONITORING OF STIMULI TO A BIOLOGICAL OBJECT, IN VITRO

(75) Inventors: Justin C. Williams, Madison, WI (US);
David J. Beebe, Monona, WI (US);
Stephen M. Johnson, Oregon, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 892 days.

(21) Appl. No.: 10/872,647

(22) Filed: Jun. 21, 2004

(65) Prior Publication Data
US 2005/0282267 A1  Dec. 22, 2005

(51) Int. Cl.
*G01N 27/403* (2006.01)
(52) U.S. Cl. .............. 422/82.01; 204/403.01; 435/287.1; 435/288.5
(58) Field of Classification Search .......... 422/82.01
See application file for complete search history.

(56) References Cited

U.S. PATENT DOCUMENTS

| | | | |
|---|---|---|---|
| 6,716,620 B2 * | 4/2004 | Bashir et al. .......... 435/287.2 |
| 6,730,199 B1 * | 5/2004 | Hanni et al. .......... 204/403.02 |
| 6,890,762 B1 * | 5/2005 | Sugihara et al. .......... 436/503 |
| 7,041,492 B2 * | 5/2006 | Oka et al. .......... 435/285.2 |
| 7,214,528 B1 * | 5/2007 | Vandenbark et al. .......... 435/283.1 |

OTHER PUBLICATIONS

"3-D Silicon Probe Array With Hybrid Polymer Interconnect For Chronic Cortical Recording," Proceedings of the 1st International IEEE EMS, Conference of Neural Engineering, Capri Island, Italy, Mar. 20-22, 2003, pp. 181-184, by J. F. Hetke, J. C. Williams, D. S. Pellinen, R. J. Vetter and D.R. Kipke.

"Lateral Propagation of EGF Signaling After Local Stimulation Is Dependent on Receptor Density," Developmental Cell, vol. 3, 245-257, Aug. 2002, Copyright 2002 by Cell Press, pp. 245-257, by A. Sawano, S. Takayama, M. Matsuda and A. Miyawaki.

* cited by examiner

*Primary Examiner*—Peter A Hruskoci
(74) *Attorney, Agent, or Firm*—Boyle Fredrickson, S.C.

(57) ABSTRACT

A micro device and method are provided for examining and testing a slice of a biological object, such as brain tissue. The micro device includes a body defining a chamber and a channel in communication with the chamber. A stimulation fluid flows axially along a flow path in the channel and engages a user selectable region of the slice. An array of electrodes in the chamber engages the slice and allows for the multi-channel electrical recording and stimulation of the slice at each of the electrode sites.

14 Claims, 6 Drawing Sheets

MICRO DEVICE FOR HIGH RESOLUTION DELIVERY AND MONITORING OF STIMULI TO A BIOLOGICAL OBJECT, IN VITRO

REFERENCE TO GOVERNMENT GRANT

This invention was made with United States government support awarded by the following agencies: DOD ARPA F30602-00-2-0570. The United States has certain rights in this invention.

FIELD OF THE INVENTION

This invention relates generally to neural recording techniques, and in particular, to a method and apparatus to monitor a large of number of neurons of a biological object in vitro while simultaneously delivering stimuli to various neuronal subpopulations with high spatial and temporal resolution.

BACKGROUND AND SUMMARY OF THE INVENTION

Under in vitro conditions, neuroscientists study neutral activities in brain tissue with single electrode intercellular and extra cellular recording techniques. By way of example, a portion of brain tissue is removed to preserve the features of interest. Once removed, the brain tissue is sliced by a microtone to produce a thin, predetermined slice of brain tissue. This resulting slice of brain tissue may be mounted on the glass slide for viewing with a microscope.

In order to analyze the brain tissue's reaction to chemical stimulation, the slice of brain tissue is often exposed to a bath of the chemical stimulus. Unfortunately, the chemical bath activates all relevant receptors in the slice of brain tissue. As such, it is difficult to ascertain the underlying cellular mechanisms that contribute to neural network reconfiguration, plasticity and behavior. Alternatively, a microinjection technique may be used wherein the chemical stimulus is localized to a specific region of the slice of brain tissue. However, as is known, microinjection techniques provide the neuroscientist with very little control over the timing and distribution of the chemical stimulus. Consequently, it is highly desirable to provide a method and apparatus that allows a neuroscientist to deliver a chemical agent to a specific region of a slice of tissue with high spatial and temporal resolution.

As is known, nerve cells, like all living cells, maintain an electrical charge across their outer membrane. By recording the electrical activity produced by the nerve cells in response to a predetermined stimulus, new discoveries in learning, memory, motor control, pain, principles of neuro network function and the like may occur. Since the electrical signals produced by nerve cells are relatively small, such electrical signals must be amplified before they can be measured accurately. In order to amplify these signals, one or more electrodes are placed adjacent the desired tissue and are operatively connected to an electronic amplifier. The size and the placement of the electrodes adjacent the brain tissue determines what aspects of neural activity will be recorded. It can be appreciated that large electrodes are utilized to record the activity of large populations of nerve cells, while small electrodes are utilized to record more localized neuroelectric events. However, as heretofore described, a high level of precision and control is necessary when interfacing with neurons, due to the dynamic timing scale of neurological events. Consequently, it is highly desirable to provide an electrode device that precisely records and/or stimulates a specific region of a slice of brain tissue for purposes of data collection and experimental control.

Therefore, it is a primary object and feature of the present invention to provide a method and apparatus capable of delivering precise amounts of chemical stimuli to neurons of a biological object with a high degree spatial and temporal resolution.

It is a further object and feature of the present invention to provide a method and apparatus for recording electrical activity from a large number of neurons in vitro while simultaneously delivering chemical stimuli to neuronal subpopulations with high spatial and temporal resolution.

It is a still further object and feature of the present invention to provide a method and apparatus for studying individual neurons in a slice of a biological object that is inexpensive and versatile.

In accordance with the present invention, a micro device is provided for examining and testing a slice of a biological object. The micro device includes a body defining a chamber therein and an electrode projecting in the chamber. The electrode has a first end for receiving the slice of the biological object thereon and a second end connectable to a monitoring device.

The body includes a base having an upper surface and a cover receivable on the upper surface of the base. The chamber extends into the base from the upper surface and terminates at a closed end. The first end of electrode lies in a plane generally co-planer with the upper surface of the base. The body also includes a flow channel in communication with the chamber and a first pulse channel communicating with the flow channel. The first pulse channel has a first input portion with an output communicating with the flow channel and a second output portion with an input communicating with the flow channel. A fluid stream flows through the flow channel and a pulse fluid flows between the output of the output portion of the first pulse channel and the input of the output portion first pulse channel.

The body may also include a second pulse channel communicating with the flow channel. The second pulse channel includes a first input portion having an output communicating with the flow channel and a second output portion having an input communicating with the flow channel. In such arrangement, the fluid stream flows through the flow channel and a first pulse fluid flows through the flow channel between the output of the output portion of the first pulse channel and the input of the output portion of the first pulse channel. The first pulse fluid has a variable cross sectional area. In addition, a second pulse fluid flows through the flow channel between the output of the output portion of the second pulse channel and the input of the output portion of the second pulse channel. The second pulse fluid also has a variable cross sectional area Further, the body may include first and second input channels. The first and second input channels have outputs communicating with the flow channel. The output of the first input channel communicates with a first side of the flow channel and the output of the second input channel communicates with a second side of the flow channel.

In accordance with a further aspect of the present invention a micro device is provided for examining and testing a biological object. The micro device includes a body defining a chamber and a channel in communication with the chamber. A stimulation fluid flows axially along a flow path in the channel. The stimulation fluid engages a user selectable region of the biological object.

It is contemplated to provide a support structure in the chamber for supporting the biological object thereon. The support structure includes an array of electrodes projecting in the chamber. At least one of the electrodes has a first end for receiving the biological object thereon. The electrodes are connectable to a monitoring device for recording electrical activity and providing stimuli to the biological object.

The micro device may also include a flow control structure for altering the flow path of the stimulation fluid such that the stimulation fluid engages the user selected region of the biological object. The flow control structure includes first and second guide fluids flowing in streams along corresponding flow paths in the channel on opposite sides of the stimulation fluid in laminar flow. The streams of the first and second guide fluids have adjustable cross-sectional areas.

The body of the micro device includes a first pulse channel communicating with the channel. The first pulse channel has a first input portion with an output communicating with the channel and a second output portion with an input communicating with the channel. A pulse fluid flows between the output of the output portion of the first pulse channel and the input of the output portion first pulse channel.

The body may also include a second pulse channel communicating with the channel. The second pulse channel includes a first input portion having an output communicating with the channel and a second output portion having an input communicating with the channel. A second pulse fluid flows through the flow channel between the output of the output portion of the second pulse channel and the input of the output portion of the second pulse channel.

In accordance with a still further aspect of the present invention, a method is provided for examining and testing a biological object. The method includes the step of positioning a slice of the biological object in a channel of a micro device. A flow of stimulation fluid is directed over a user selected region of the slice. The flow of stimulation fluid may be constant or defined by a series of pulses of the stimulation fluid, such as a chemical agent.

The method may also include the additional step of supporting the slice on an array of electrodes. Electrical activity may be sensed at predetermined regions of the slice with the electrodes. In addition, a predetermined region of the slice may be stimulated with at least one of the electrodes.

The step of directing the flow of stimulation fluid may include the additional step of providing first and second guide fluids having variable cross sectional areas in the channel on opposite sides of the stimulation fluid. The first and second guide fluids and the stimulation fluid flow along corresponding axial flow paths in laminar flow. The cross sectional area of at least one guide fluid is varied so as to alter the axial flow path of the stimulation fluid.

The method of the present invention may include the additional step of stopping the flow of stimulation fluid. The step of stopping the stimulation fluid includes the additional step of providing first and second guide fluids having variable cross sectional areas in the channel on opposite sides of the stimulation fluid. The first and second guide fluids and the stimulation fluid flow along corresponding axial flow paths in laminar flow. Thereafter, the cross sectional area of at least one guide fluid is varied so as prevent the stimulation fluid for flowing therepast.

BRIEF DESCRIPTION OF THE DRAWINGS

The drawings furnished herewith illustrate a preferred construction of the present invention in which the above advantages and features are clearly disclosed as well as others which will be readily understood from the following description of the illustrated embodiment.

In the drawings.

DETAILED DESCRIPTION OF THE DRAWINGS

Figure 1:
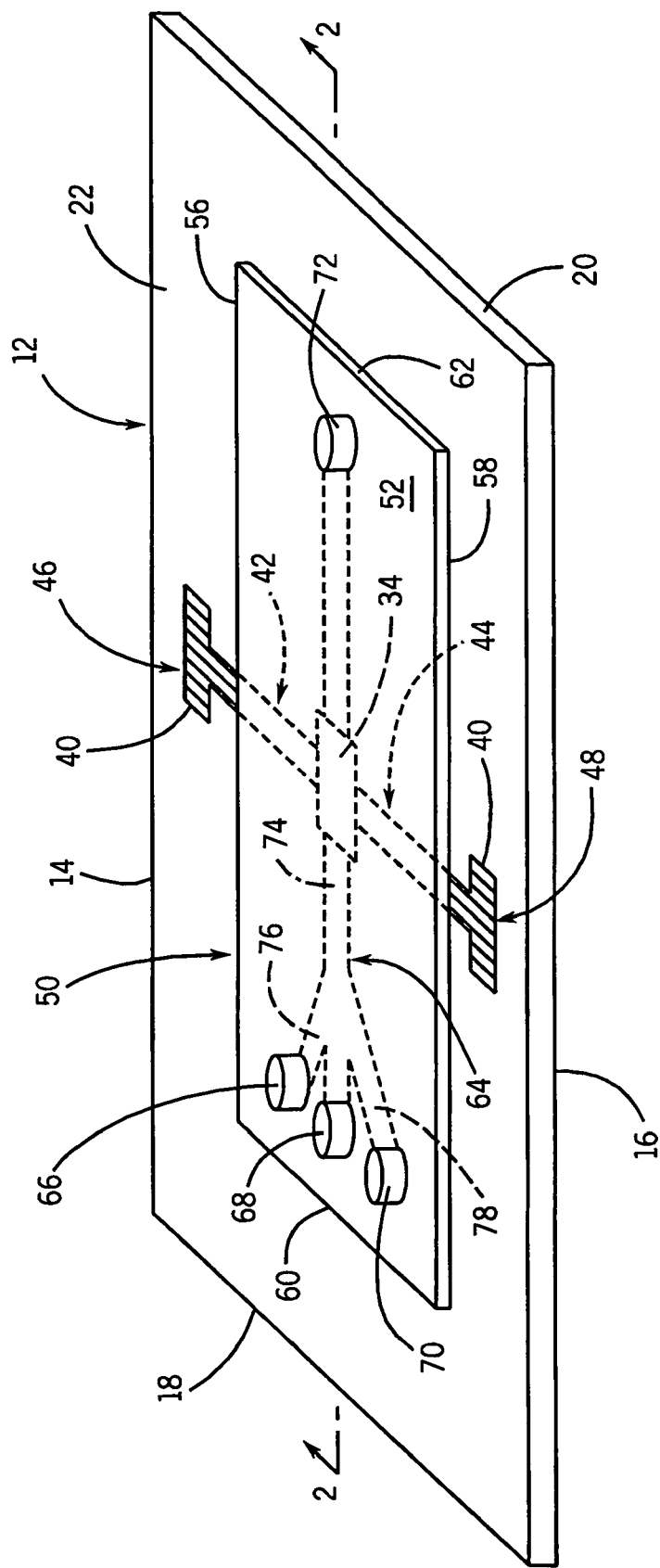
FIG. 1 is an isometric view of a micro device in accordance with the present invention.
Figure 2:
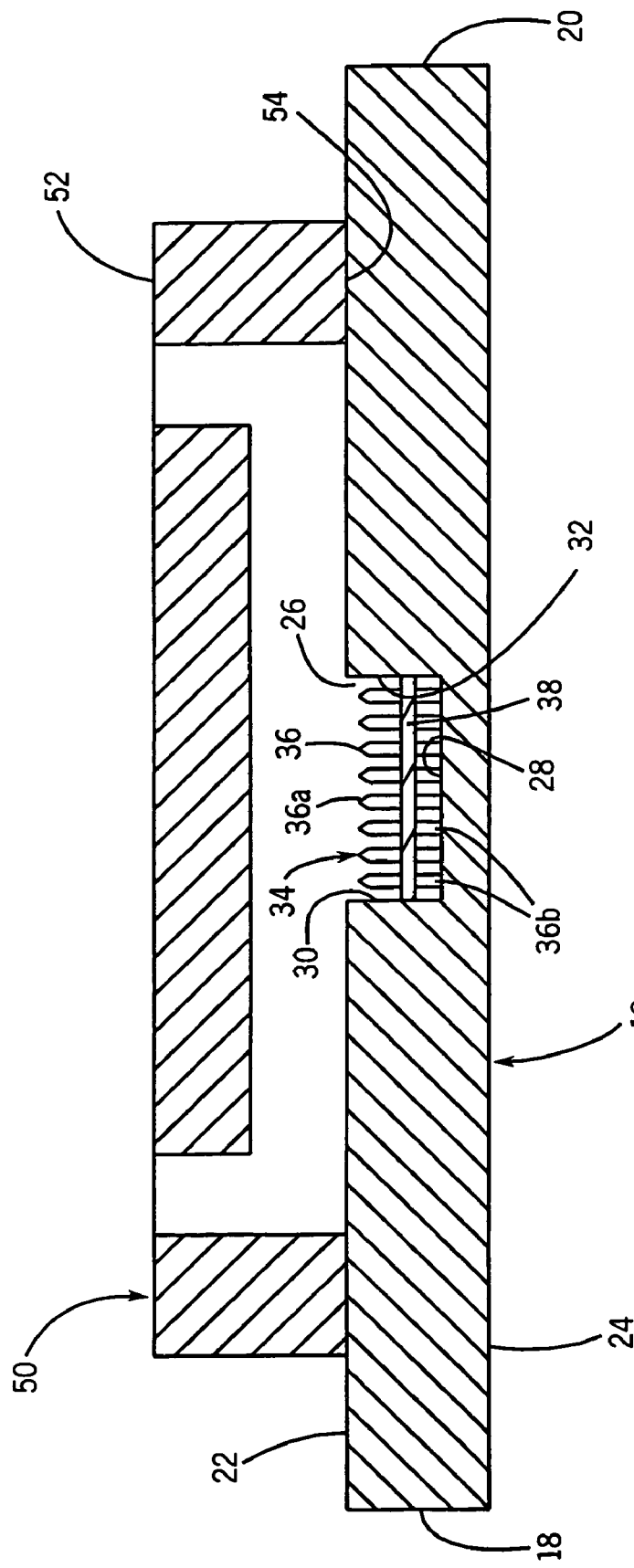
FIG. 2 is a cross-sectional view of the micro device of FIG. 1 taken along line 2-2.
Figure 3:
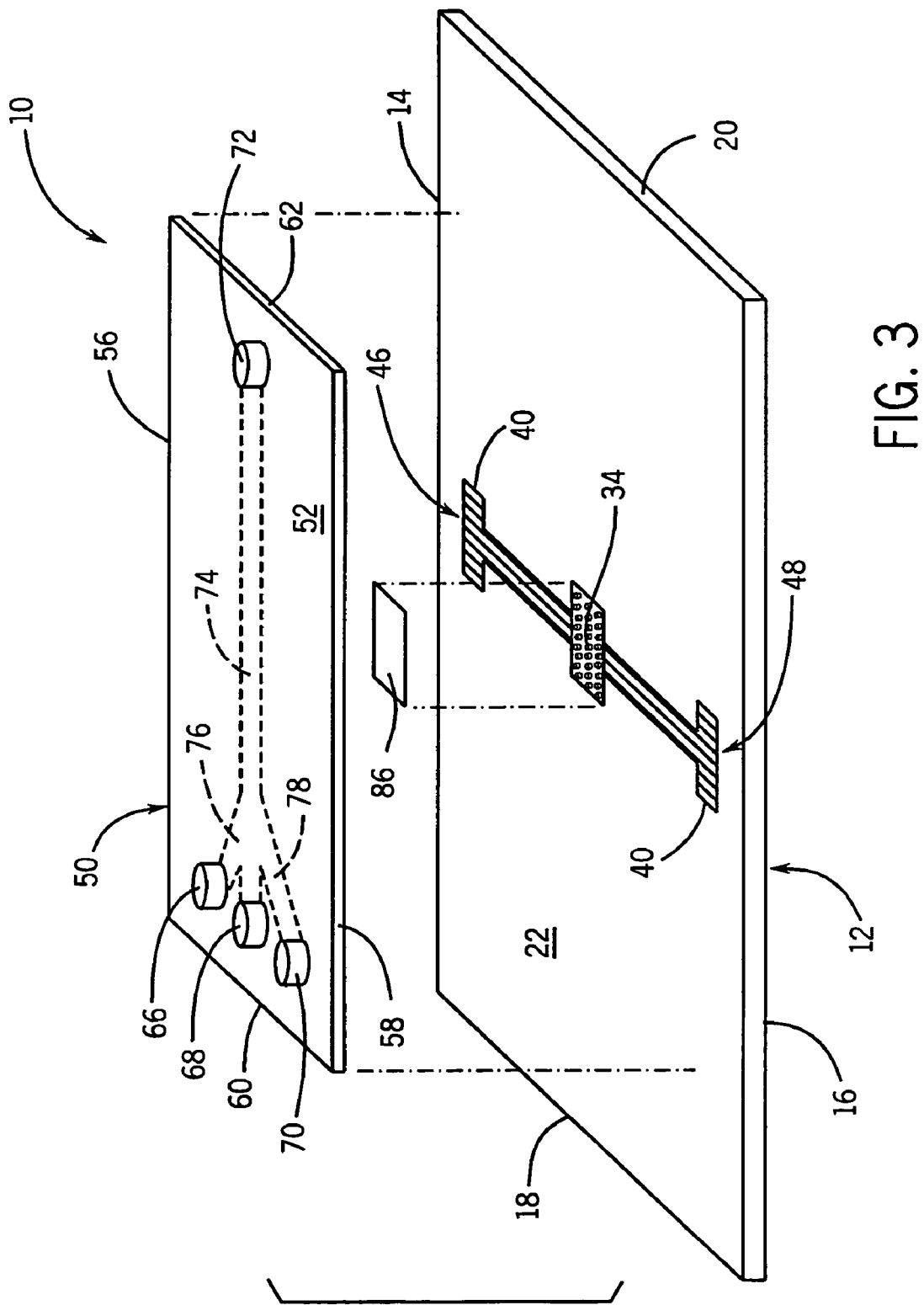
FIG. 3 is an exploded, isometric view of the micro device of the present invention.
Figure 4:
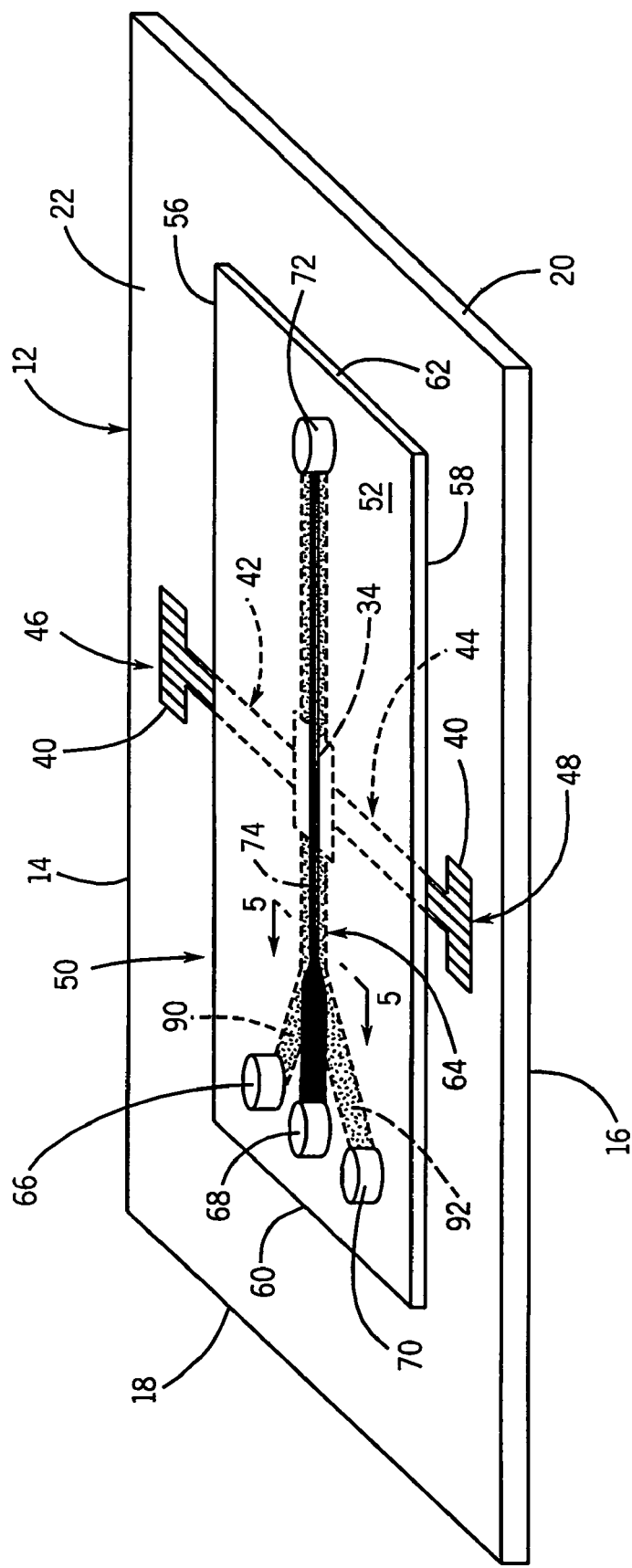
FIG. 4 is an isometric view of the micro device of FIG. 1 effectuating a portion of the method of the present invention.

Referring to FIG. 1 and FIG. 2, a micro device in accordance with the present invention is generally designated by the reference numeral 10. Micro device 10 includes a generally flat slide 12 defined by first and second generally parallel slides 14 and 16, respectively, and first and second ends 18 and 20, respectively. In the depicted embodiment, slide 12 has a generally rectangular configuration, however, other configurations are possible without deviating from the scope of the present invention. Slide 12 further includes a generally flat upper surface 22 and a generally flat lower surface 24. As best seen in FIG. 2, recess 26 is provided in upper surface 22 of slide 12. Recess 26 in upper surface 22 of slide 12 is defined by recessed surface 28 spaced from upper surface 22 by vertical side walls 30 and 32. Recess 26 is adapted for receiving a three dimensional electrode array generally designated by the reference numeral 34.

Electrode array 34 includes a plurality of electrodes 36 extending through a generally rectangular handling platform 38. Electrodes 36 include upper terminal ends 36a that lie in a plane generally co-planar with or slightly below upper surface 22 of slide 12. Lower ends 36b of electrodes 36 are interconnected to corresponding cables 40 in any suitable manner such as by rivet bonds or the like. First and second portions 42 and 44, respectively, of cables 40 diverge laterally from electrode array 34 toward corresponding sides 14 and 16, respectively, of slide 12 along upper surface 22 thereof. First and second portions 42 and 44, respectively, of cables 40 terminate at corresponding connection pads 46 and 48, respectively. Connection pads 46 and 48 may be electrically connected to a central processing unit (not shown) so as to allow for multi-channel electrical recording and stimulation at each of the electrode sites within recess 26 of upper surface 22 of slide 12.

Micro device 10 further includes cover 50 having generally flat upper and lower surfaces 52 and 54, respectively, interconnected by first and second sides 56 and 58, respectively, and first and second ends 60 and 62, respectively. In the depicted embodiment, cover 50 has a generally rectangular configuration. However, it can be appreciated that cover 50 may take on other configurations without deviating from the scope of the present invention. Cover 50 further includes one or more channel networks 64 which may be used to effectuate the method of the present invention. It is noted that the configuration of channel network 64 may be altered without deviating from the scope of the present invention.

Figure 5:
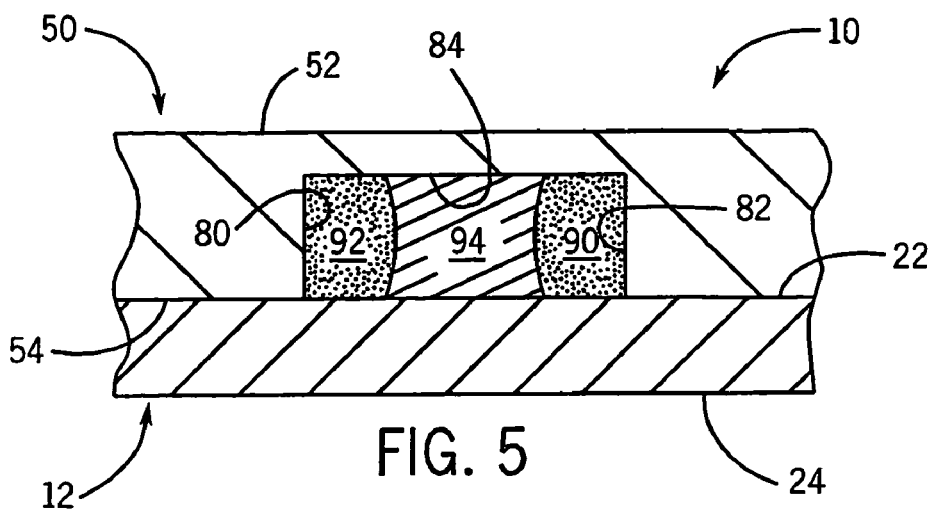
FIG. 5 is a cross-sectional view of the micro device of FIG. 4 taken along line 5-5 depicting first and second virtual walls in a first position flowing in a central channel to control the flow of chemical stimuli therethrough.

As best seen in FIGS. 1-4, channel network 64 is generally Y-shaped and includes inputs 66, 68 and 70 for a pulse fluid and fluid stream and output 72 communicating with and depending from upper surface of cover 50. In addition, channel network 64 includes central channel or flow channel 74, as well as, first and second input or pulse channels 76 and 78, respectively. Central channel 74 extends along an axis and communicates with input 68 and output 72. As best seen in FIG. 5, central channel 74 is defined by first and second spaced sidewalls 80 and 82, respectively, extending into cover 50 from lower surface 54 thereof and upper wall 84 such that central channel 74 has a generally square cross-section. With cover 50 positioned on upper surface 22 of slice 12, central channel 74 defines a passageway through micro device 10 that communicates with recess 26 in upper surface 22 of slice 12, for reason hereinafter described. It is noted that other configurations of central channel 74 are possible without deviating from the scope of the present invention.

First input channel 76 has a first end communicating with input 66 and a second end communicating with central channel 74. First input 66 may be connected to a first fluid source for providing a first fluid to channel network 64. Similarly, second input passageway 78 has a first end communicating with input 70 and a second end communicating with central passageway 74. Second input 70 may be connected to a second fluid source for providing a second fluid to channel network 64.

In order to assemble micro device 10, slide 12 is positioned on a generally flat surface. A biological object such as slice 86 of brain tissue is deposited on terminal ends 36a of electrodes 36. While it is contemplated for the present invention to be used in connection with slice 86 of brain tissue, it can be appreciated that other types biological objects and/or slices of biological objects may be used without deviating from the scope of the present invention. By way of example, the biological object may take the form of a cultured neural tissue comprising dissociated neural cells, neural stem cells and/or transgenic neural cells. Once slice 86 is deposited on terminal ends 36a of electrodes 36, cover 50 is deposited on upper surface 22 of slide 12 such that terminal ends 36a of the electrodes 36 communicate with central channel 74 in cover 50. Connection pads 46 and 48 are electrically connected to a central processing unit (not shown) so as to allow multichannel electrical recordings and stimulation of slice 86 by each of the electrodes 36 within recess 26 of upper surface 22 of slide 12.

In order to direct a predetermined chemical or non-chemical (e.g., temperature) stimuli over a desired region of slice 86, the principles of multi-stream laminar flow are utilized. Referring to FIGS. 4-7, by way of example, first and second guide fluids 90 and 92, respectively, may be provided at corresponding inputs 66 and 70, respectively, such that guide fluids 90 and 92 flow in corresponding streams through input channels 76 and 78, respectively, into central channel 74 toward output 72. In addition, stimuli 94 may be provided at input 68 such that chemical stimuli 94 flows in a stream through central channel 74 towards output 72 thereby communicating with slice 86. Due to the fact that the streams of guide fluids 90 and 92 and the stream of stimuli 94 are flowing in central channel 74 in smooth laminar flow, without turbulence, the streams can flow together without mixing with each other.

Figure 6:
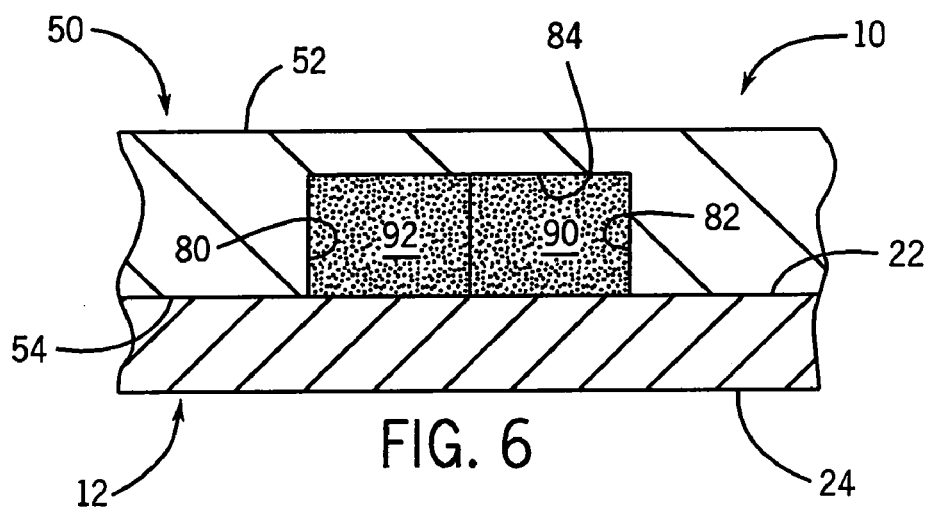
FIG. 6 is a cross-sectional view of the micro device of the present invention, similar to FIG. 5, depicting the first and second virtual walls in a second position.
Figure 7:
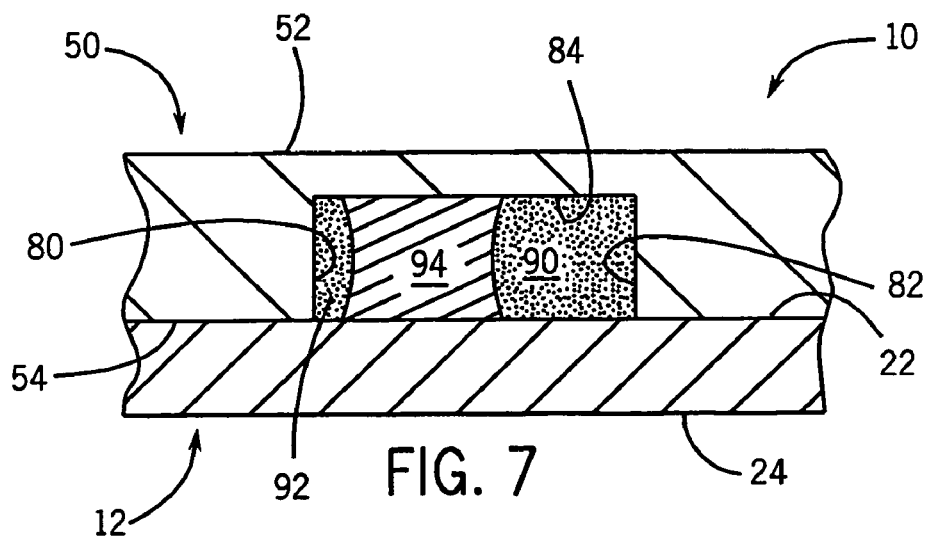
FIG. 7 is a cross-sectional view of the micro device of the present invention, similar to FIG. 5, depicting the first and second virtual walls in a third position.

As best seen in FIGS. 6-7, by varying the pressure of the guide fluids 90 and 92 provided at inputs 66 and 70, respectively, of micro device 10, the cross sectional areas of the streams of guide fluids 90 and 92 flowing through central channel 74 may be increased or decreased. Referring to FIG. 6, by increasing the pressure of both guide fluids 90 and 92 provided at inputs 66 and 70, respectively, of micro device 10, the cross sectional areas of the streams of guide fluids 90 and 92 flowing through central channel 74 are increased, thereby narrowing the cross sectional area of the stream of stimuli 94. It can be appreciated that the cross sectional areas of the streams of guide fluids 90 and 92 flowing through central channel 74 may be increased to such a point that the streams expand and contact each other, thereby preventing stimuli 94 from continuing to flow downstream and contacting slice 86.

Alternatively, the pressure of one of the guide fluids 90 and 92 provided at inputs 66 and 70, respectively, of micro device 10, may be increased while the pressure of the other of the guide fluids 90 and 92 may be decreased. Referring to FIG. 7, by way of example, the pressure of guide fluid 90 provided at input 66 of micro device 10 is increased such that the cross sectional area of the stream of guide fluid 90 flowing through central channel 74 increases. In addition, the pressure of guide fluid 92 provided at input 70 of micro device 10 is decreased such that the cross sectional area of the stream of guide fluid 92 flowing through central channel 74 decreases. As a result, it can be appreciated that the stream of stimuli 94 flowing through central channel 74 is moved laterally towards sidewall 80, thereby exposing a different region of slice 86 to stimuli 94 flowing through central channel 74. In such a manner, a neuroscientist can vary the axial flow path of stimuli 94 so as deliver stimuli 94 to various neuronal subpopulations on slice 86 with high spatial resolution.

Figure 8:
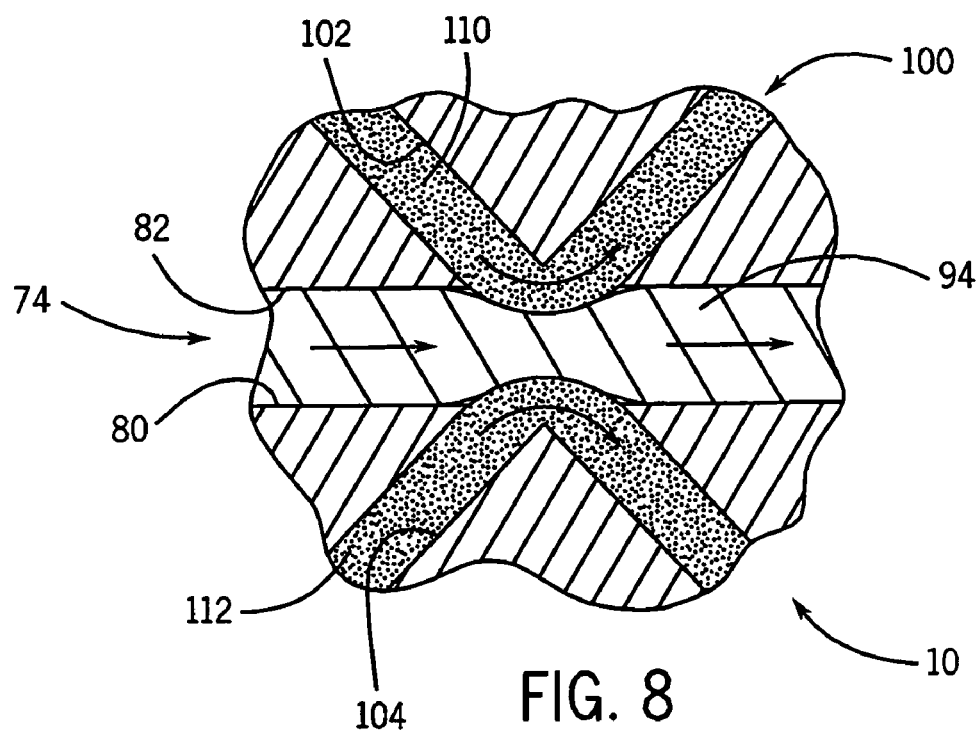
FIG. 8 is a cross-sectional view showing a X valve in an open position for use with the micro device of FIG. 1.
Figure 9:
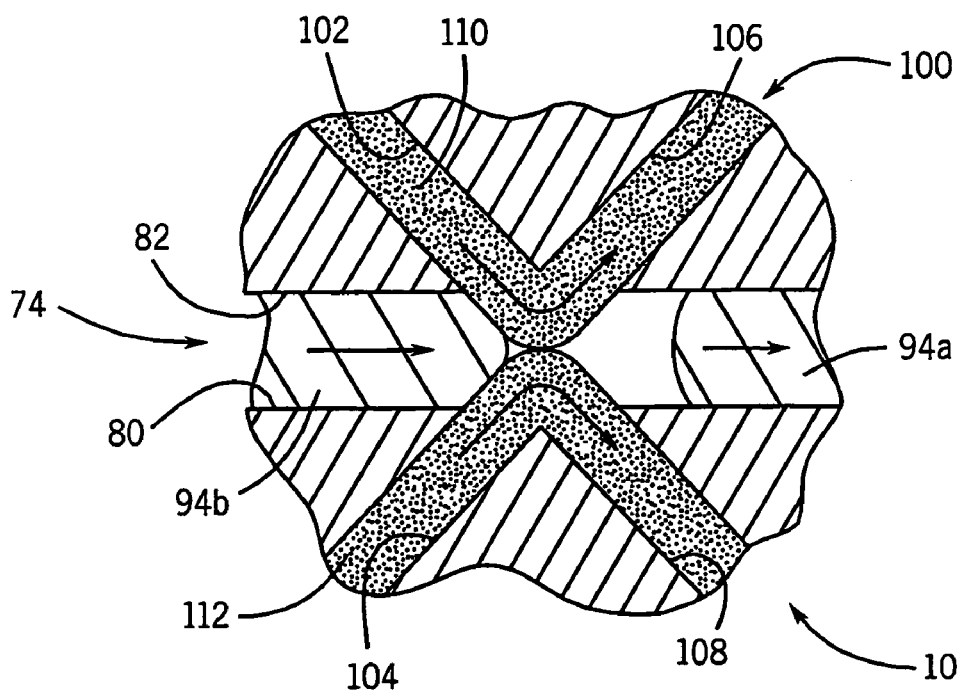
FIG. 9 is a cross-sectional view showing the X valve of FIG. 8 in a closed position.

While not depicted in the Figures, it can be understood that additional input channels may be provided in micro device 10 so as to allow for additional streams of the same or different stimuli to flow through central channel 74. In the matter heretofore described, the precise location of the streams may varied so as to simultaneously expose different, user selected regions of slice 86 to the same or different stimuli. Further, it is completed to provide various functional components such as mixers, valves, filters, and sensors in central channel 74 upstream of electrode array 34, and hence slice 86, to facilitate the ease of use, rapid reconfiguration and reproducibility of micro device 10. By way of example, referring to FIGS. 8-9, x-valve 100 is provided for hydrodynamically focusing the stream of stimuli 94 to flow across slice 86 at a user desired location and for generating a pulsed stream of stimuli 94 for engaging slice 86 with a high degree of temporal resolution.

X-valve 100 is defined by first input channel 102 having a first end communicating with a first fluid source and a second end communicating with central channel 74, and second input channel 104 having a first end communicating a second fluid source and a second end communicating with central channel 74. In addition, x-valve 100 includes first output channel 106 having a first end communicating with central channel 74 and a second end, and second output channel 108 having a first end communicating with central channel 74 and a second end.

In operation, with stimuli 94 flowing in central channel 74, as heretofore described, first and second guide fluids 110 and 112, respectively, may be provided at first ends of corresponding input channels 102 and 104, respectively, such that streams of guide fluids 110 and 112 flow into central channel 74. Due to the principles of laminar flow, it can be understood that the streams of guide fluids 110 and 112 in central channel 74 will be urged toward and into the first ends of corresponding output channels 106 and 108, respectively. Due to the fact that the streams of guide fluids 110 and 112 and the stream of stimuli 94 are flowing in central channel 74 in smooth laminar flow, without turbulence, the streams can flow together without mixing with each other.

As heretofore described, by varying the pressure of the guide fluids 110 and 112 provided to input channels 102 and 104, respectively, the cross sectional areas of the portions of the streams of guide fluids 110 and 112 flowing through central channel 74 may be increased or decreased. By increasing the pressure of both guide fluids 110 and 112, the cross sectional areas of the portions of the streams of guide fluids 110 and 112 flowing through central channel 74 are increased, thereby narrowing the cross sectional area of the stream of stimuli 94. It can be appreciated that the cross sectional areas of the portions of the streams of guide fluids 110 and 112 flowing through central channel 74 may be increased to such a point that the streams expand and contact each other, thereby prevent stimuli 94 from continuing to flow downstream and contacting slice 86, FIG. 9. Consequently, by sequentially increase and decreasing the pressures of guide fluids 110 and 112 provided to input channels 102 and 104, respectively, over a predetermined time period, a series of pulses 94a and 94b of stimuli 94 made be produced. This, in turn, allows for slice 86 to be sequentially exposed to pulses 94a and 94b of stimuli 94 with a high degree of temporal resolution.

In addition, it is contemplated to vary the pressures of the guide fluids 110 and 112 provided to input channels 102 and 104, respectively, in order to vary the axial flow path of the stream of stimuli 94, thereby allowing a neuroscientist the ability to expose user selected regions of slice 86 to stimuli 94. By way of example, the pressure of guide fluid 110 provided to input channel 102 may increased such that the cross sectional area of the stream of guide fluid 110 flowing through central channel 74 increases. In addition, the pressure of guide fluid 112 provided to input channel 104 may be decreased such that the cross sectional area of the stream of guide fluid 112 flowing through central channel 74 decreases. As a result, it can be appreciated that the flow path of the stream of stimuli 94 flowing through central channel 74 is moved laterally towards sidewall 80, thereby exposing a different region of slice 86 to stimuli 94. In such manner, a neuroscientist can vary the axial flow path of stimuli 94 so as deliver stimuli 94 to various neuronal subpopulations on slice 86 with high spatial resolution.

By utilizing multiple parallel independent laminar fluid streams, in combination with various functional components such as x-valve 100, actuators, pumps, filters, and like, a hydrodynamically focused stream of stimuli 94 may be provided to flow across a user desired region of slice 86, while being pulsed with high temporal resolution. As heretofore described, this high level of control is necessary when interfacing with neurons, due to the dynamic time scale of neurological events. Further, by providing independent, focused streams of stimuli, multiple forms of stimuli can be delivered to different regions of slice 86 and/or specific regions of slice 86 can be deprived of nutrients for a precise period of time, while simultaneously providing other regions of slice 86 with pulses 94a and 94b of stimuli 94. This, in turn, provides limitless potential for a neuroscientist to rapidly and reversibly expose specific regions of a neural network to different drugs, in various combinations, at different doses and within a timeframe of milliseconds to minutes, in vitro.

Various modes of carrying out the invention are contemplated as being within the scope of the following claims particularly pointing out and distinctly claiming the subject matter, which is regarded as the invention.

We claim:

1. A micro device for examination and testing of a biological object, comprising:
   a body defining a chamber therein, the body includes:
      a flow channel in communication with the chamber; and
      a first pulse channel communicating with the flow channel, the first pulse channel including a first input portion having an output communicating with the flow channel and a second output portion having an input communicating with the flow channel; and
   an electrode projecting in the chamber, the electrode having a first end for receiving the biological object thereon and a second end connectable to a monitoring device;
   a fluid stream flowing through the flow channel; and
   a pulse fluid flowing between the output of the output portion of the first pulse channel and the input of the output portion, wherein the body includes a second pulse channel communicating with the flow channel, the second pulse channel including a first input portion having an output communicating with the flow channel and a second output portion having an input communicating with the flow channel.

2. The micro device of claim 1 wherein the body includes a base having an upper surface and a cover receivable on the upper surface of the base.

3. The micro device of claim 2 wherein the chamber extends into the base from the upper surface and terminates at a closed end and wherein the first end of electrode lies in a plane generally co-planer with the upper surface.

4. The micro device of claim 1 further comprising:
   a fluid stream flowing through the flow channel;
   a first pulse fluid flowing through the flow channel between the output of the output portion of the first pulse channel and the input of the output portion of the first pulse channel, the first pulse fluid having a variable cross sectional area; and
   a second pulse fluid flowing through the flow channel between the output of the output portion of the second pulse channel and the input of the output portion of the second pulse channel, the second pulse fluid having a variable cross sectional area.

5. The micro device of claim 1 wherein the electrode is one of an array of electrodes connectable to the monitoring device.

6. A micro device for examination and testing of a biological object, comprising:
   a body defining:
      a chamber; and
      a channel in communication with the chamber;
   an array of electrodes projecting in the chamber, at least one of the electrodes having a first end for receiving the biological object thereon; and
   a stimulation fluid flowing axially along a flow path in the channel, the stimulation fluid capable of engaging different user selectable regions of the biological object to the same or different stimuli.

7. The micro device of claim 6 wherein the electrodes are connectable to a monitoring device for recording electrical activity and providing stimuli to the biological object.

8. The micro device of claim 6 further comprising a flow control structure for altering the flow path of the stimulation fluid such that the stimulation fluid engages the user selected region of the biological object.

9. The micro device of claim 6 wherein the body includes a first pulse channel communicating with the channel, the first pulse channel including a first input portion having an output communicating with the channel and a second output portion having an input communicating with the channel.

10. The micro device of claim 9 further comprising:
a pulse fluid flowing between the output of the output portion of the first pulse channel and the input of the output portion of the first pulse channel.

11. A micro device for examination and testing of a biological object, comprising:
a body defining a chamber therein, the body includes:
a flow channel in communication with the chamber; and
first and second input channels, the first and second input channels having outputs communicating with the flow channel; and
an electrode projecting in the chamber, the electrode having a first end for receiving the biological object thereon and a second end connectable to a monitoring device;
wherein the output of the first input channel communicates with a first side of the flow channel and the output of the second input channel communicates with a second side of the flow channel and wherein the flow channel includes an input upstream of the output of the first input channel.

12. A micro device for examination and testing of a biological object, comprising:
a body defining:
a chamber; and
a channel in communication with the chamber;
an array of electrodes projecting in the chamber, at least one of the electrodes having a first end for receiving the biological object thereon;
a stimulation fluid flowing axially along a flow path in the channel, the stimulation fluid engaging a user selectable region of the biological object; and
a flow control structure for altering the flow path of the stimulation fluid such that the stimulation fluid engages the user selected region of the biological object, the flow control structure includes first and second guide fluids flowing in streams along corresponding flow paths in the channel on opposite sides of the stimulation fluid in laminar flow, the streams of the first and second guide fluids having adjustable cross-sectional areas.

13. A micro device for examination and testing of a biological object, comprising:
a body defining:
a chamber;
a channel in communication with the chamber;
a first pulse channel communicating with the channel, the first pulse channel including a first input portion having an output communicating with the channel and a second output portion having an input communicating with the channel; and
a second pulse channel communicating with the channel, the second pulse channel including a first input portion having an output communicating with the channel and a second output portion having an input communicating with the channel;
an array of electrodes projecting in the chamber, at least one of the electrodes having a first end for receiving the biological object thereon; and
a stimulation fluid flowing axially along a flow path in the channel, the stimulation fluid engaging a user selectable region of the biological object.

14. The micro device of claim 13 further comprising:
a first pulse fluid flowing through the channel between the output of the output portion of the first pulse channel and the input of the output portion of the first pulse channel, the first pulse fluid having a variable cross section area; and
a second pulse fluid flowing through the channel between the output of the output portion of the second pulse channel and the input of the output portion of the second pulse channel, the second pulse fluid having a variable cross section area.

* * * * *